United States Patent [19]

Knutson et al.

[11] Patent Number: 5,602,116
[45] Date of Patent: Feb. 11, 1997

[54] METHOD FOR TREATING AND PREVENTING SECONDARY HYPERPARATHYROIDISM

[75] Inventors: Joyce C. Knutson, Madison; Charles W. Bishop, Verona; Richard B. Mazess, Madison, all of Wis.

[73] Assignee: Bone Care International, Inc., Madison, Wis.

[21] Appl. No.: 415,488

[22] Filed: Apr. 3, 1995

Related U.S. Application Data

[63] Continuation-in-part of Ser. No. 119,895, Sep. 10, 1993, Pat. No. 5,403,831, which is a continuation of Ser. No. 812,056, Mar. 5, 1992, abandoned, which is a continuation of Ser. No. 569,412, Aug. 17, 1990, Pat. No. 5,104,864, which is a continuation of Ser. No. 227,371, Aug. 2, 1988, abandoned.

[51] Int. Cl.$^6$ ............................................. A61K 31/59
[52] U.S. Cl. ................................... 514/167; 552/653
[58] Field of Search .......................... 514/167; 552/653

[56] References Cited

U.S. PATENT DOCUMENTS

| | | | |
|---|---|---|---|
| 3,907,843 | 9/1975 | DeLuca et al. | 260/397.2 |
| 4,195,027 | 3/1980 | De Luca et al. | 260/397.2 |
| 4,202,829 | 5/1980 | DeLuca et al. | 260/397.2 |
| 4,234,495 | 11/1980 | DeLuca et al. | 260/397.2 |
| 4,260,549 | 4/1981 | DeLuca et al. | 260/397.2 |
| 4,554,106 | 11/1985 | DeLuca et al. | 260/397.2 |
| 4,555,364 | 11/1985 | DeLuca et al. | 260/397.2 |
| 5,063,221 | 11/1991 | Nishii et al. | 514/167 |

OTHER PUBLICATIONS

G. F. Jensen et al., *Clin. Endocrinol.* 16, 515–524 (1982).
C. Christiansen et al., *Eur. J. Clin. Invest.* 11, 305–309 (1981).
O. H. Sorensen et al., *Clin. Endocrinol.* 7, 169S–175S (1977).
H. Orimo et al., *Bone and Mineral* 3, 47–52 (1987).
G. Sjoden et al., *J. Nutr.* 114, 2043–2046 (1984).
G. Sjoden et al., *Proc. Soc. Exp. Biol. Med.* 178, 432–436 (1985).
*The Merck Index*, 11th ed. (1989) p. 9932.
*J. Bone Min. Res.*; 1994; 9:607–614.
M. F. Holick et al., *Proc. Natl. Acad. Sci. USA* 68, 803–804 (1971).
G. Jones et al., *Biochemistry* 14, 1250–1256 (1975).
M. F. Holick et al., *Science* 180, 190, 191 (1973).
H. Y. Lam et al., *Science* 486, 1038–1040 (1974).
S. M. Ott, C. H. Chestnut, *Annals of Int. Med.* 1989, 110:267–274.
J. C. Gallagher et al., *Annals of Int. Med.* 1990, 113:649–655.
J. Aloia et al., *Amer. J. Med.* 84:401–08 (1988).
M. Shiraki et al., *Endocrinol. Japan* 32, 305–315 (1985).

*Primary Examiner*—Theodore J. Criares
*Attorney, Agent, or Firm*—Teresa J. Welch; Stroud, Stroud, Willink, Thompson & Howard

[57] ABSTRACT

A method for preventing loss of bone mass or bone mineral content in a human being suffering from secondary hyperparathyroidism by administering a sufficient amount of 1α-OH vitamin $D_2$, 1α,24(S)-(OH)$_2$ vitamin $D_2$, 1α-OH vitamin $D_4$ or 1α,24(R)-(OH)$_2$ vitamin $D_4$.

9 Claims, No Drawings

METHOD FOR TREATING AND PREVENTING SECONDARY HYPERPARATHYROIDISM

This application is a continuation in part of Ser. No. 08/119,895, Sep. 10, 1993, now U.S. Pat. No. 5,403,831, which is a continuation of Ser. No. 07/812,056, Mar. 5, 1992, now abandoned, which is a continuation of Ser. No. 07/569,412, Aug. 17, 1990, now U.S. Pat. No. 5,104,864, which is a continuation of Ser. No. 07/227,371, Aug. 2, 1988, now abandoned.

TECHNICAL FIELD

This invention relates generally to methods for treating and preventing metabolic bone disorders characterized by loss of bone mass or by disproportionately low bone mineral content. More specifically, this invention relates to a method for treating or preventing hyperparathyroidism secondary to end-stage renal disease, one of the concomitant results of which is the loss of bone mass or decreased mineral content (i.e., renal osteodystrophy).

BACKGROUND OF THE INVENTION

Numerous metabolic bone disorders are known which are characterized by loss of bone mass or bone mineral. These disorders include postmenopausal osteoporosis, senile osteoporosis, corticosteroid-induced osteopenia, anticonvulsant osteomalacia and renal osteodystrophy. Of these disorders, renal osteodystrophy is encountered in end-stage renal disease patients undergoing chronic dialysis.

As a group, these bone depletive disorders are a major and growing public health problem in the United States. Together, they cause more than 1 million bone fractures per year, primarily of the spine, hip, and distal forearm, and result in an annual cost above $10 billion to the American society. Unfortunately, the incidence of these bone disorders will rise significantly as the mean age of the U.S. population continues to increase.

Despite differing etiologies, the aforementioned metabolic bone disorders develop during an extended period of negative calcium balance. This commonality of the disorders suggests that agents which stimulate intestinal calcium absorption and otherwise regulate calcium homeostasis may be effective in restoring calcium balance, thereby treating or preventing the development of such bone disorders.

It has long been known that vitamin D plays a critical role in stimulating calcium absorption and regulating calcium metabolism. The discovery of the active forms of vitamin D in the 1970's [M. F. Holick et al., *Proc. Natl. Acad. Sci. USA* 68, 803–804 (1971); G. Jones et al., *Biochemistry* 14, 1250–1256 (1975)] and active vitamin D analogues [M. F. Holick et al., *Science* 180, 190, 191 (1973); H. Y. Lam et al., *Science* 186, 1038–1040 (1974)], caused much excitement and speculation about the usefulness of these compounds in the treatment of bone depletive disorders.

Animal and early clinical studies examining the effects of these active vitamin D compounds suggested that such agents would be useful in restoring calcium balance. However, the best indicator of the efficacy of vitamin D compounds to prevent or treat depletive bone disorders is bone itself (or, in the case of renal osteodystrophy, serum levels of parathyroid hormone (PTH)) rather than calcium absorption or calcium balance. Certain clinical studies with $1\alpha,25\text{-}(OH)_2$ vitamin $D_3$, and $1\alpha\text{-}OH$ vitamin $D_3$ indicate that the ability of these agents to restore lost bone mass or bone mineral content is dose related. [See, S. M. Ott, C. H. Chesnut, *Annals of Int. Med.* 1989; 110:267–274; J. C. Gallagher et al., *Annals of Int. Med.* 1990; 113:649–655; J. Aloia et al., *Amer. J. Med.* 84:401–08 (1988)] M. Shiraki et al., *Endocrinol. Japan* 32, 305–315 (1985)].

These studies also indicate that at the dosage ranges required for these agents to be truly effective, toxicity in the form of hypercalcemia and hypercalciuria becomes a major problem. Attempts to increase the amount of $1\alpha,25\text{-}(OH)_2$ vitamin $D_3$ above 0.5 μg/day have frequently resulted in toxicity. At dosage levels below 0.5 μg/day, clinically significant effects are rarely observed on bone. [See G. F. Jensen et al., *Clin. Endocrinol.* 16, 515–524 (1982); C. Christiansen et al., *Eur. J. Clin.* Invest. 11, 305–309 (1981)]. Doses of 2 μg/day of $1\alpha\text{-}OH$ vitamin $D_3$ were found to have efficacy in increasing bone mass in patients exhibiting senile osteoporosis [O. H. Sorensen et al., *Clin. Endocrinol.* 7, 169S–175S (1977)]. Data from clinical studies in Japan, a population that has low calcium intake, indicate that efficacy is found with $1\alpha\text{-}OH$ vitamin $D_3$ when administered at 1 μg/day [M. Shiraki et al., *Endocrinol. Japan.* 32:305–315 (1985); H. Orimo et al., *Bone and Mineral* 3, 47–52 (1987)]. However, at 2 μg/day, toxicity with $1\alpha\text{-}OH$ vitamin $D_3$ occurs in approximately 67 percent of the patients, and at 1 μg/day this percentage is approximately 20 percent.

Thus, the prior art teaches that due to their toxicity, 1-hydroxylated vitamin D compounds can only be administered at dosages that are, at best, modestly beneficial in preventing or treating loss of bone or bone mineral content. Indeed, Aloia recommends that alternative routes of administration be sought which might avoid the toxicity problems and allow higher dosage levels to be achieved. [J. Aloia et al., *Amer. J. Med.* 84:401–408 (1988)].

Despite reported toxicities of $1\alpha\text{-}OH$ vitamin $D_3$ and $1\alpha,25\text{-}(OH)_2$ vitamin $D_3$, these two compounds remain the drugs of choice for many bone depletive disease treatments. For example, in end stage renal disease, these two drugs remain the only approved forms of $1\alpha$-hydroxylated vitamin D for treating or preventing secondary hyperparathyroidism, although both drugs are not currently approved in all major pharmaceutical markets.

At present, in the United States, end stage renal disease afflicts approximately 200,000 individuals. In this disease, there is a progressive loss of cells of the proximal nephrons, the primary site for the synthesis of the vitamin D hormones (collectively "$1\alpha,25\text{-}(OH)_2D$") from 25-hydroxyvitamin $D_3$ and 25-hydroxyvitamin $D_2$. In addition, the loss of functioning nephrons leads to retention of excess phosphorus which reduces the activity of the renal 25-hydroxyvitamin D-$1\alpha$-hydroxylase, the enzyme which catalyzes the reaction to produce the D hormones. These two events account for the low serum levels of $1\alpha,25\text{-}(OH)_2D$ commonly found in patients with mild to moderate end stage renal disease.

Reduced serum levels of $1\alpha,25\text{-}(OH)_2D$ cause increased, and ultimately excessive, secretion of PTH by direct and indirect mechanisms. The resulting hyperparathyroidism leads to markedly increased bone turnover and its sequela of renal osteodystrophy, which may include a variety of other diseases, such as, osteitis fibrosa cystica, osteomalacia, osteoporosis, extraskeletal calcification and related disorders, e.g., bone pain, periarticular inflammation and Mockerberg's sclerosis. Reduced serum levels of $1\alpha,25\text{-}(OH)_2D$ also can cause muscle weakness and growth retardation with skeletal deformities (most often seen in pediatric patients).

All previous clinical studies of hormonally active vitamin D drugs in end stage renal disease patients have focused exclusively on compounds derived from vitamin $D_3$. Use of $1\alpha,25\text{-}(OH)_2D_3$ and $1\alpha\text{-}OH\text{-vitamin }D_3$ as replacement therapy seeks to treat or prevent renal osteodystrophy by treating or preventing secondary hyperparathyroidism in end stage renal disease patients. As noted above, $1\alpha,25\text{-}(OH)_2D_3$ often causes toxic side effects (hypercalcemia and hyperphosphatemia) at dosages above 0.5 µg, especially when concomitantly administered calcium phosphate binders are used to control serum phosphorus. The minimum effective dose for preventing secondary hyperparathyroidism is in the range of 0.25 to 0.50 µg/day; most patients respond to oral treatment doses of 0.5 to 1.0 µg/day or intravenous doses between 0.5 and 3.0 µg three times per week. As described above, the other commonly used vitamin D drug is $1\alpha\text{-}OH\text{-}D_3$ which often causes toxic effects at dosages over 1.0 µg/day, especially when used with calcium phosphate binders. The minimum effective dosage for preventing secondary hyperparathyroidism is in the range of 0.25 to 1.0 µg/day, and most patients require treatment dosages of 1.0 µg/day or more. When either drug, $1\alpha,25\text{-}(OH)_2D_3$ or $1\alpha\text{-}OH\text{-}D_3$, is administered in higher dosages, both efficacy and toxicity are found to increase. Thus, the hormonally active vitamin $D_3$ compounds are limited in their therapeutic usefulness due to their inherent toxicities.

To reduce the incidence of toxic side effects with $1\alpha,25\text{-}(OH)_2D_3$ or $1\alpha\text{-}OH\text{-}D_3$, a low calcium dialysate with an ionized calcium concentration of 1.25 mM has been developed. However, it has been found that use of the low calcium dialysate has lead to higher serum PTH and phosphorus levels in patients who do not receive increased doses of oral calcium supplements and phosphate binders. When the dosages of calcium supplements and phosphate binders are increased, serum levels of phosphorus become controlled, but the incidence of hypercalcemia rises markedly. Thus, there are many problems associated with the use of current vitamin D therapies for secondary hyperparathyroidism.

Notwithstanding these known problems with use of the hormonally active vitamin $D_3$ for secondary hyperparathyroidism, the art has not adequately responded to date with the introduction of other vitamin compounds, derivatives or analogs that possess less inherent toxicity.

SUMMARY OF THE INVENTION

The present invention provides a method for treating or preventing hyperparathyroidism secondary to end stage renal disease by lowering (or maintaining low) serum parathyroid hormone levels in a patient suffering from the disease. The method at the same time ameliorates or prevents the renal osteodystrophy which can develop in such patients.

The foregoing, and other advantages of the present invention, are realized in one aspect thereof in a method for lowering serum (or plasma) PTH in patients suffering from hyperparathyroidism secondary to end stage renal disease, comprising: administering to these patients an effective amount of a vitamin D analog of formula (I), as described hereinbelow, to lower the serum PTH level. The analog of formula (I) is any active vitamin D compound which has potent biological activity but low calcemic activity relative to the active forms of vitamin $D_3$. Preferably such compounds are $1\alpha\text{-}OH\text{-vitamin }D_2$; $1\alpha,24(S)\text{-}(OH)_2\text{-vitamin }D_2$; $1\alpha\text{-}OH\text{-vitamin }D_4$; or $1\alpha,24(R)\text{-}(OH)_2\text{-vitamin }D_4$. The analog of formula (I) is administered in a dosage amount of 1 to about 100 µg/week. As used herein, the term "vitamin D analog" is meant to refer to compounds having vitamin D hormonal bioactivity. It is also noted that a shorthand notation is often used for the D hormones, e.g., $1\alpha\text{-hydroxy}$ vitamin $D_2$ may be referred to as $1\alpha\text{-}OH\text{-vitamin }D_2$ or simply $1\alpha\text{-}OH\text{-}D_2$.

In another aspect, the invention is a pharmaceutical composition having serum (or plasma) PTH lowering activity, which includes, in unit dosage form, an effective amount of a vitamin D analog which is $1\alpha\text{-}OH\text{-vitamin }D_2$ $1\alpha,24(S)\text{-}(OH)_2\text{-vitamin }D_2$; $1\alpha\text{-}OH\text{-vitamin }D_4$; or $1\alpha,24(R)\text{-}(OH)_2\text{-}$ vitamin $D_4$; and a pharmaceutically acceptable excipient.

The treatment method of the present invention is an alternative to conventional therapy with $1\alpha,25\text{-}(OH)_2$ vitamin $D_3$ or $1\alpha\text{-}OH\text{-vitamin }D_3$; the method is characterized by providing an active vitamin D compound having equivalent bioactivity but much lower toxicity than these conventional therapies. This is true especially in the case where oral calcium phosphate binders are used concomitantly to control serum phosphorus. As such, the method addresses a long felt need in secondary hyperparathyroidism therapy.

A comparison of $1\alpha\text{-}OH\text{-vitamin }D_2$ to $1\alpha\text{-}OH\text{-vitamin }D_3$ has been conducted. $1\alpha\text{-}OH\text{-vitamin }D_2$ is equally active as $1\alpha\text{-}OH\text{-vitamin }D_3$ in the healing of rickets, in the stimulation of intestinal calcium absorption and in the elevation of serum inorganic phosphorous of rachitic rats. [G. Sjoden et al., *J. Nutr.* 114, 2043–2946 (1984)]. In the same laboratory animal, the inventors also have found that $1\alpha\text{-}OH\text{-vitamin }D_2$ is 5 to 15 times less toxic than $1\alpha\text{-}OH\text{-}$ vitamin $D_3$ [see, also, G. Sjoden et al., *Proc. Soc. Exp. Biol. Med.* 178, 432–436 (1985)]. It has now been found that, for example, $1\alpha\text{-}OH\text{-vitamin }D_2$ may be safely administered for up to two years to human subjects experiencing or having a tendency toward loss of bone mass or bone mineral content at dosages greater than 3 µg/day.

The present invention is also intended to be used in all bone depletive disorders which respond to administration of active forms of vitamin D.

Other advantages and a fuller appreciation of specific adaptations, compositional variations, and physical attributes will be gained upon an examination of the following derailed description of preferred embodiments.

DETAILED DESCRIPTION

The present invention relates broadly to bone depletive disorders. However, the method of the present invention is most particularly adapted for use in ameliorating or preventing hyperparathyroidism secondary to end stage renal disease. The method also ameliorates or prevents the concomitant renal osteodystrophy of these patients with this disease. Accordingly, the present invention will now be described in detail with respect to such endeavors; however, those skilled in the art will appreciate that such a description of the invention is meant to be exemplary only and should not be viewed as limitative on the full scope thereof.

More specifically, the present invention relates to therapeutic methods for lowering the excessively high blood levels of parathyroid hormone (PTH) which are secondary to end stage renal disease. The method in accordance with the present invention has significantly less resultant hypercalcemia and hyperphosphatemia, especially in patients who use oral calcium phosphate binders to control serum phosphorus levels. These attributes are achieved through a novel treatment of a patient suffering from secondary hyperparathyroidism with a vitamin D analog of formula (I) as described hereinbelow.

In accordance with the invention, it has been found that when the analogs of formula (I) are administered to end stage renal disease patients with elevated serum parathyroid hormone, PTH concentration is lowered with significantly less hypercalcemia and hyperphosphatemia than is observed after the same amount of activated vitamin D administered in previously known formulations. Thus, the compounds of formula (I) have an improved therapeutic index relative to vitamin $D_3$ analogs.

The vitamin D analogs in accordance with the present invention have the general formula:

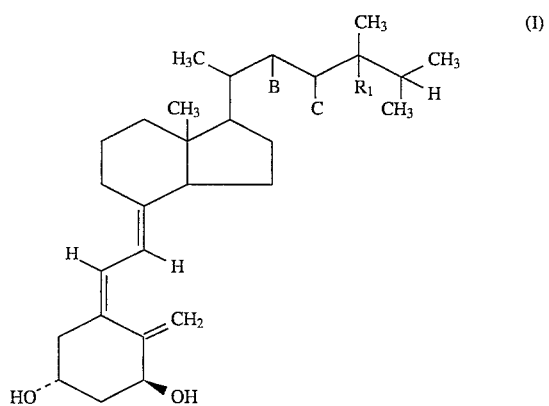

where B and C are each either H or together form a carbon—carbon double bond, and where $R_1$ is either a hydrogen or hydroxyl. The analogs of formula (I) are substantially less toxic than their vitamin $D_3$ counterparts when administered to patients experiencing hyperparathyroidism secondary to end stage renal disease. For patients using oral calcium phosphate binders, administration of the analogs of formula (I) at dosage levels higher than possible with the vitamin $D_3$ compounds provides greater efficacy than heretofore possible in treating secondary hyperparathyroidism.

Preferred among the analogs of formula (I) are: 1α-hydroxyvitamin $D_2$ (also known as 1α-hydroxyergocalciferol); 1α-hydroxyvitamin $D_4$; 1α,24(S)-dihydroxyvitamin $D_2$ and 1α,24(R)-dihydroxyvitamin $D_4$. Most preferred is 1α-hydroxyvitamin $D_2$, a prodrug for 1α,25-dihydroxyvitamin $D_2$ which is an endogenous metabolite of vitamin $D_2$.

It is noted that the medical community currently views vitamin $D_3$ compounds as biologically indistinguishable from the corresponding vitamin $D_2$ compounds. This is evident from the indiscriminate inclusion of either vitamin $D_2$ or $D_3$ in vitamin supplements prepared for human use, and from the interchangeable use of either vitamin in treating bone diseases caused by vitamin D deficiency. Curiously, medical experts consider the hormonally active forms of the two vitamins to be equivalent despite lack of confirmation from a single human study. (It is also interestingly noted that vitamin $D_4$ is described in *The Merck Index* (Merck Index, 11th ed. (1989) p. 9932) as having doubtful biological activity.)

In parent application, Ser. No. 08/119,895 and its parent application, now U.S. Pat. No. 5,104,864, it has been shown that 1α-OH-vitamin $D_2$ has the same biopotency as 1α-OH-vitamin $D_3$ and 1α,25-$(OH)_2$-vitamin $D_3$ but is much less toxic. Even dosages up to 10 µg/day of 1α-OH-vitamin $D_2$ in women with postmenopausal osteoporosis (in both open label and double blind testing) exhibited only mild hypercalciuria (>300 mg/24 hrs), and marked hypercalcemia (>11.0 mg/dL) solely due to 1α-OH-vitamin $D_2$ was not evident. Additionally, the compound did not adversely affect kidney function, as determined by creatinine clearance and BUN; nor did it increase urinary excretion of hydroxyproline, indicating the absence of any stimulatory effect on bone resorption. Administration of 1α-OH-vitamin $D_2$ to healthy adult males in dosages up to 8 µg/day showed no hypercalcemia or other adverse effects.

The analogs of formula (I) are useful as active compounds in pharmaceutical compositions. The pharmacologically active analogs of this invention can be processed in accordance with conventional methods of pharmacy to produce pharmaceutical agents for administration to patients, e.g., in admixtures with conventional excipients such as pharmaceutically acceptable organic or inorganic carrier substances suitable for parenteral, enteral (e.g., oral) or topical application which do not deleteriously react with the active compounds. Suitable pharmaceutically acceptable carriers include but are not limited to water, salt (buffer) solutions, alcohols, gum arabic, mineral and vegetable oils, benzyl alcohols, polyethylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic active compounds. If a solid carrier is used, the dosage form of the analogs may be tablets, capsules, powders, suppositories, or lozenges. If a liquid carrier is used, soft gelatin capsules, transdermal patches, aerosol sprays, topical creams, syrups or liquid suspensions, emulsions or solutions may be the dosage form.

For parenteral application, particularly suitable are injectable, sterile solutions, preferably oily or aqueous solutions, as well as suspensions, emulsions, or implants, including suppositories. Ampoules are convenient unit dosages. The dosage of the analogs in accordance with the present invention for parenteral administration generally is about 1–30 µg given 1 to 3 times per week.

For enteral application, particularly suitable are tablets, dragées, liquids, drops, suppositories, or capsules. A syrup, elixir, or the like can be used wherein a sweetened vehicle is employed.

Sustained or directed release compositions can be formulated, e.g., liposomes or those wherein the active compound is protected with differentially degradable coatings, e.g., by microencapsulation, multiple coatings, etc. It is also possible to freeze-dry the new compounds and use the lypolizates obtained, for example, for the preparation of products for injection.

For topical application, there are employed as nonsprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, etc.

Oral administration is preferred. Generally, the analogs of this invention are dispensed by unit dosage form comprising about 0.25 to about 5.0 µg in a pharmaceutically acceptable carrier per unit dosage. The dosage of the analogs according to this invention generally is about 1 to about 100 µg/week, preferably about 3 to about 25 µg/week.

It will be appreciated that the actual preferred amounts of active analog in a specific case will vary according to the specific compound being utilized, the particular compositions formulated, the mode of application, and the particular situs being treated. Dosages can be determined using conventional considerations, e.g., by customary comparison of the differential activities of the subject compounds and of a known agent, e.g. by means of an appropriate conventional pharmacological protocol.

The specific doses for each particular patient depend on a wide variety of factors, for example, on the efficacy of the specific compound employed, on the age, body weight, general state of health, sex, on the diet, on the timing and mode of administration, on the rate of excretion, and on medicaments used in combination and the severity of the particular disorder to which the therapy is applied.

It is possible, if desired, to produce the metabolites of certain ones of the analogs of formula (I), in particular by nonchemical means. For this purpose, it is possible to convert them into a suitable form for administration together with at least one vehicle or auxiliary and, where appropriate, combined with one or more other active compounds.

The dosage forms may also contain adjuvants, such as preserving or stabilizing adjuvants. They may also contain other therapeutically valuable substances or may contain more than one of the compounds specified herein and in the claims in admixture.

Bulk quantities of the vitamin D analogs for the practice of this invention can be readily obtained in accordance with the processes of U.S. Pat. Nos. 3,907,843; 4,195,027; 4,202,829; 4,234,495; 4,260,549; 4,555,364; and 4,554,106 and U.S. patent application Ser. Nos. 08/275,641 and 08/296,084.

As described hereinbefore, the analogs of formula (I) are preferably administered to the human patients in oral dosage formulation. As an analog in accordance with the present invention is released from the oral dosage formulation, it is absorbed from the intestine into the blood.

The present invention is further explained by the following examples which should not be construed by way of limiting the scope of the present invention.

EXAMPLE 1

Study Demonstrating Better Safety

The low toxicity of 1α-OH-vitamin $D_2$ in human patients was demonstrated in a clinical study involving 15 postmenopausal osteoporotic women. [J. Bone Min. Res.; 1994; 9:607–614.] The selected patients were between 55 and 75 years of age, and exhibited L2–L3 vertebral bone mineral density ("BMD") between 0.7 and 1.05 g/cm², as determined by measurements with a LUNAR dual-photon absorptiometer. (The mean bone mineral density in women with osteoporosis is about 0.85±0.17 g/cm², so that these limits correspond to about the 15th to 85th percentiles.)

On admission to the study, all patients received instruction on selecting a daily diet containing 400 to 600 mg of calcium. Compliance to this diet was verified at weekly intervals by 24-hour food records and by interviews with each patient.

All patients completed a one-week baseline period, a five- to seven-week treatment period, and a one-week post-treatment observation period. During the treatment period, patients orally self-administered 1α-OH-vitamin $D_2$ at an initial dose of 0.5 µg/day for the first week, and at successively higher doses of 1.0, 2.0, 4.0, 5.0, 8.0 and 10.0 µg/day in each of the following weeks. All doses were administered before breakfast.

Blood and urine chemistries were monitored on a weekly basis throughout the study. Key blood chemistries included fasting serum levels of calcium, phosphorus, osteocalcin, creatinine and blood urea nitrogen. Key urine chemistries included 24-hour excretion of calcium, phosphorous and creatinine.

Data from the study clearly demonstrated that 1α-OH-vitamin $D_2$ can be safely administered for short periods at high dose levels. In particular, the compound did not adversely affect kidney function, as determined by creatinine clearance and blood levels of urea nitrogen; nor did it increase urinary excretion of hydroxyproline, indicating the absence of any stimulatory effect on bone resorption. The compound had no effect on any routinely monitored serum chemistries, indicating the absence of adverse metabolic effects.

A positive effect of 1α-OH-vitamin $D_2$ on calcium homeostasis was evident from dose-related increases observed in 24-hour urinary calcium levels, confirming that the compound increases intestinal calcium absorption, and from dose-related increases in serum osteocalcin, suggesting that the compound directly stimulates bone formation.

EXAMPLE 2

Study Demonstrating Safety and Efficacy for Human Osteoporosis

The safety and efficacy of 1α-OH-vitamin $D_2$ as an oral treatment for osteoporosis was confirmed in a study involving 60 postmenopausal osteoporotic outpatients. The selected subjects had ages between 60 and 70 years, and exhibited L2–L3 vertebral BMD between 0.7 and 1.05 g/cm², as determined by dual-energy x-ray absorptiometry (DEXA). Exclusion criteria encompassed significant medical disorders and recent use of medications known to affect bone or calcium metabolism.

On admission to the study, each subject was assigned at random to one of two treatment groups; one group received up to a 104-week course of therapy with 1α-OH-vitamin $D_2$; the other received only placebo therapy. All subjects received instruction on selecting a daily diet containing 700–900 mg of calcium and were advised to adhere to this diet over the course of the study. Compliance to the diet was verified at regular intervals by 24-hour food records and by interviews with each subject.

During the treatment period, subjects from one group orally self-administered 1α-OH-vitamin $D_2$ at an initial dosage of 1.0 µg/day for one week, and increased the dosage to 2.0, 3.0, 4.0 µg/day in each of the following weeks, to a maximum dosage of 5.0 µg/day. The dosage for any given subject was increased in this way until the rate of urinary calcium excretion was elevated to approximately 275–300 mg/24 hours, at which point the subject held the dosage constant at the highest level attained. Subjects from the second group self-administered a matching placebo medication every day, titrating the apparent dosage upwards in the same manner as subjects being treated with 1α-OH-vitamin $D_2$.

Spinal and femoral neck BMD were measured in all subjects by DEXA at the beginning of the study, and at six-month intervals thereafter. Intestinal calcium absorption was estimated in all subjects by a single isotope technique at the beginning of the study, and at 12-month intervals. Serum levels of vitamin D metabolites were determined by radioreceptor binding assays at baseline and at six-month intervals.

Serum osteocalcin, serum PTH and urine hydroxyproline also were determined at baseline and at six-month intervals.

Other blood and urine chemistries were monitored at regular intervals during the treatment period. These chemistries included serum calcium, serum ionized calcium, urine calcium, blood urea nitrogen, serum creatinine and creatinine clearance. Kidney-ureter-bladder (KUB) x-rays were obtained at baseline and at 12-month intervals thereafter.

The results of the study are summarized below:

Subjects: Sixty subjects enrolled in what was originally intended to be a 52-week study. Of these 60 subjects, 55 completed one year of treatment (28 active; 27 placebo); and 41 subjects completed an optional second year of treatment.

Test Drug Dosages: The average prescribed dosage for subjects who received 1α-OH-vitamin $D_2$ was 4.2 μg/day at 52 weeks and 3.6 μg/day at 104 weeks. The average prescribed dosage for placebo subjects was an apparent 4.8 μg/day at 52 weeks and 4.8 μg/day at 104 weeks.

Exclusions: One subject failed to comply with the prescribed dosage of test drug, as confirmed by an absence of serum 1α,25-dihydroxyvitamin $D_2$ at any time during the study. Data for this subject were excluded from analysis. Three patients were diagnosed with hyperparathyroidism when the PTH assays were completed (in batch) at the study's conclusion; data for these subjects were excluded from analysis. No subjects were excluded from analysis for noncompliance with the required dietary calcium intake of 700–900 mg/day.

Episodes of Hypercalcemia/Hypercalciuria: Marked hypercalcemia (>10.8 mg/dL) occurred in one subject in association with an intercurrent illnes. The prescribed dosage of 1α-OH-vitamin $D_2$ at the time of this episode was 5.0 μg/day. Moderate hypercalcemia (10.4–10.8 mg/dL) occurred in two subjects over the course of the study at prescribed dosages of 5.0 μg/day. Mild hypercalcemia (10.2–10.4 mg/dL) occurred in four subjects in the first year, and in two subjects in the second year. Hypercalciuria was observed occasionally over the two-year study in 17 subjects treated with 1α-OH-vitamin $D_2$.

Serum Calcium/Ionized Calcium: Mean serum calcium was approximately 0.1 to 0.2 mg/dL higher in subjects treated with 1α-OH-vitamin $D_2$ than in subjects treated with placebo. This difference was significant (P<0.05) only during the second year of treatment. Mean serum ionized calcium was approximately 0.05 to 0.10 mg/dL higher in subjects treated with 1α-OH-vitamin $D_2$.

Urine Calcium: Mean urine calcium increased during the initial titration period in a dose-response fashion. After titration, mean urine calcium was 50 to 130% higher (P<001) with 1α-OH-vitamin $D_2$ treatment than with placebo treatment.

Kidney Function: No significant changes were observed with long-term 1α-OH-vitamin $D_2$ treatment in BUN, serum creatinine or creatinine clearance. KUB x-rays revealed no abnormalities in either treatment group throughout the course of the study.

Bone: Bone mineral density (BMD) in the L2–L4 vertebrae progressively increased with 1α-OH-vitamin $D_2$ treatment and decreased with placebo treatment over the two-year study. The difference in spinal BMD between the treatment groups became statistically significant (P<0.05) after 24 months of treatment. Similar changes were observed in femoral neck BMD with statistically significant differences observed after 18 months (P<0.001) and 24 months (P<0.05) of treatment.

Calcium Uptake: Intestinal absorption of orally administered $^{45}Ca$ increased by 40% (P<0.001) after 52 weeks of 1α-OH-vitamin $D_2$ therapy, and by 29% (P<0.5) after 104 weeks of 1α-OH-vitamin $D_2$ therapy, relative to placebo control.

Vitamin D Metabolites: Treatment with 1α-OH-vitamin $D_2$ caused progressive increases in mean serum total 1α,25-dyhydroxyvitamin D from 21% (P<0.05) at six months to 49% (P<0.01) at 24 months relative to placebo therapy. This increase resulted from a dramatic rise in serum 1α,25-dihydroxyvitamin $D_2$ which was partially offset by a 50+% decrease in serum 1α,25-dihydroxyvitamin $D_3$. No treatment related changes were apparent in serum total 25-hydroxyvitamin D.

Biochemical Parameters:

Serum levels of PTH decreased with 1α-OH-vitamin $D_2$ therapy by 17% at 52 weeks and by 25% at 1–4 weeks, relative to placebo therapy.

Serum levels of osteocalcin were unchanged with long-term 1α-OH-vitamin $D_2$ therapy.

Fasting urine hydroxyproline:creatinine ratio tended to decrease with long-term 1α-OH-vitamin $D_2$ treatment but the observed differences between the 1α-OH-vitamin $D_2$ and placebo treatment groups were not significantly different.

The results of this study clearly indicated that 1α-OH-vitamin $D_2$ can be tolerated in higher long-term dosages than the commonly used vitamin $D_3$ analogues. They also showed that 1α-OH-vitamin $D_2$ is well tolerated in postmenopausal women at long-term dosages in the range of 2.0 to 3.0 μg/day, provided that individuals exhibiting abnormally high urine calcium levels (when not receiving vitamin D therapy) are excluded from treatment. Long-term administration of such high dosages of 1α-OH-vitamin $D_2$ significantly reduced bone loss at the spine and femoral neck, the most frequent sites of osteoporotic fractures. These positive effects on bone were accompanied by a sustained increase in intestinal calcium absorption and a sustained decrease in serum PTH. They were not accompanied by clear long-term trends in serum osteocalcin and urine hydroxyproline. Taken together, the results of this study demonstrate that 1α-OH-vitamin $D_2$ is safe and effective in the treatment of postmenopausal or senile osteoporosis.

EXAMPLE 3

Open Label Study in End Stage Renal Disease Patients Exhibiting Secondary Hyperparathyroidism Five end stage renal disease patients were enrolled in an open label study. The selected patients had ages between 36 and 72 years and had been on hemodialysis for at least 4 months prior to enrollment. The patients each had an average serum phosphorus in the range of 3.0 to less than or equal to 6.9 mg/dL during the two months prior to enrollment (often controlled by oral calcium phosphate binders), and had a history of elevated serum PTH values of greater than 400 pg/mL when not receiving 1α,25-$(OH)_2$-vitamin $D_3$ therapy.

Each patient had been receiving 1α,25-$(OH)_2$ vitamin $D_3$ prior to enrollment, and discontinued the 1α,25-$(OH)_2$ vitamin $D_3$ therapy for eight weeks prior to receiving 1α-OH-vitamin $D_2$. After 8 weeks, the patients received treatment of 1α-OH-vitamin $D_2$ at a dosage of 4 μg/day for 6 weeks. Throughout the eight-week washout period and the treatment period, patients were monitored weekly or biweekly for serum intact PTH level and weekly for excessive elevation in serum levels of calcium and phosphorus.

Throughout the washout period and treatment period, patients underwent routine hemodialysis (3 times per week) using a 1.25 mM calcium dialysate. They also ingested significant amounts of calcium phosphate binders (1–10 g elemental Ca) to keep serum phosphorus levels below 6.9 mg/dL.

Baseline serum PTH was 480±21; SCa (mg/dl), 9.8±0.3 and serum phosphorus (mg/dl), 5.1±0.2. In three patients, serum PTH decreased by 68%, 74% and 87% after two weeks. In the other two patients, serum PTH declined by 33% in one and 3% in the other after four weeks. Overall, serum PTH decreased by 49±17% and 33±9% after two and four weeks of 1α-OH-vitamin $D_2$, respectively, (p<0.05). Serum calcium was 10.2±0.4 (p<0.05) and 9.8±0.2 (NS) and serum phosphorus was 5.4±0.5 and 5.5±0.8 at two and four weeks, respectively (NS). A rise in serum PTH from the second to fourth weeks of 1α-OH-vitamin $D_2$ occurred when 1α-OH-vitamin $D_2$ was withheld in three patients with serum PTH<130; they developed mild hypercalcemia (serum calcium, 10.3–11.4) that reversed after stopping 1α-OH-vitamin $D_2$. No other adverse effects occurred. At 4–6 weeks of 1α-OH-vitamin $D_2$ treatment of 4 µg, thrice weekly, four of five patients were in the target range of serum PTH; serum calcium was 10.0±0.2 and serum phosphorus, 5.3±0.2 mg/dl. The patient who failed to respond to six weeks of 1α-OH-vitamin $D_2$ treatment had a delayed response to both intravenous and oral calcitriol earlier, requiring several months of treatment before serum PTH fell. Serum PTH values in this patient fell by 38% after eight weeks of 1α-OH-vitamin $D_2$ treatment. These dates show that 1α-OH-vitamin $D_2$ is efficacious and safe for the control of secondary hyperparathyroidism in end stage renal disease patients.

EXAMPLE 4

Double Blind Study of Bone in End Stage Renal Disease Patients

A twelve-month double-blind placebo-controlled clinical trial is conducted with thirty-five men and women with renal disease who are undergoing chronic hemodialysis. All patients enter an eight-week control period during which time they receive a maintenance dose of vitamin $D_3$ (400 IU/day). After this control period, the patients are randomized into two treatment groups: one group receives a constant dosage of 1α-OH-vitamin D: (u.i.d.; a dosage greater than 3.0 µg/day) and the other group receives a matching placebo. Both treatment groups receive a maintenance dosage of vitamin $D_3$, maintain a normal intake of dietary calcium, and refrain from using calcium supplements. Oral calcium phosphate binders are used as necessary to maintain serum levels of phosphorus below 7.0 mg/dL. Efficacy is evaluated by pre- and post-treatment comparisons of the two patient groups with regard to (a) direct measurements of intestinal calcium absorption, (b) total body calcium retention, (c) radial and spinal bone mineral density, and (d) determinations of serum calcium and osteocalcin. Safety is evaluated by regular monitoring of serum calcium.

Analysis of the clinical data show that 1α-OH-vitamin $D_2$ significantly increases serum osteocalcin levels and intestinal calcium absorption, as determined by direct measurement using a double-isotope technique. Patients treated with this compound show normalized serum calcium levels, stable values for total body calcium, and stable radial and spinal bone densities relative to baseline values. In contrast, patients treated with placebo show frequent hypocalcemia, significant reductions in total body calcium and radial and spinal bone density. An insignificant incidence of hypercalcemia is observed in the treated group.

EXAMPLE 5

Double-blind Study in End Stage Renal Disease (ESRD) Patients Exhibiting Secondary Hyperparathyroidism Up to 120 ESRD (End Stage Renal Disease) patients undergoing chronic hemodialysis are studied in a multi-center, double-blind, placebo-controlled study based in two major U.S. metropolitan areas. The selected patients reside in two major metropolitan areas within the continental U.S., have ages between 20 and 75 years and have a history of secondary hyperparathyroidism. They have been on hemodialysis for at least four months, have a normal (or near normal) serum albumin, and have controlled serum phosphorus (often by using oral calcium phosphate binders).

On admission to the study, each patient is assigned at random to one of two treatment groups. One of these groups receives two consecutive 12-week courses of therapy with 1α-OH-vitamin $D_2$; the other receives a 12-week course of therapy with 1α-OH-vitamin $D_2$ followed, without interruption, by a 12-week course of placebo therapy. Each patient discontinues any 1α,25-OH$_2$-vitamin $D_3$ therapy for eight weeks prior to initiating 1α-OH-vitamin $D_2$ therapy (4 µg/day). Throughout this eight-week washout (or control) period and the two subsequent 12-week treatment periods, patients are monitored weekly for serum calcium and phosphorus. Serum intact PTH is monitored weekly or biweekly, and bone-specific serum markers, serum vitamin D metabolites, serum albumin, blood chemistries, hemoglobin and hematocrit are monitored at selected intervals.

During the study, patients undergo routine hemodialysis (three times per week) using a 1.24 mM calcium dialysate and ingest calcium phosphate binders (such as calcium carbonate or calcium acetate) in an amount sufficient to keep serum phosphate controlled (≦6.9 mg/dL). Patients who develop persistent mild hypercalcemia or mild hyperphosphatemia during the treatment periods reduce their 1α-OH-vitamin $D_2$ dosage to 4 µg three times per week (or lower). Patients who develop marked hypercalcemia or marked hyperphosphatemia immediately suspend treatment. Such patients are monitored at twice weekly intervals until the serum calcium or phosphorus is normalized, and resume 1α-OH-vitamin $D_2$ dosing at a rate which is 4 µg three times per week (or lower).

During the eight-week washout period, the mean serum level of PTH increases progressively and significantly. After initiation of 1α-(OH)-vitamin $D_2$ dosing, mean serum PTH decreases significantly to less than 50% of pretreatment levels. Due to this drop in serum PTH, some patients need to reduce their dosage of 1α-OH-vitamin $D_2$ to 4 µg three times per week (or to even lower levels) to prevent excessive suppression of serum PTH. In such patients, exhibiting excessive suppression of serum PTH, transient mild hypercalcemia is observed, which is corrected by appropriate reductions in 1α-OH-vitamin $D_2$ dosages.

At the end of the first 12-week treatment period, mean serum PTH is in the desired range of 130 to 240 pg/mL and serum levels of calcium and phosphorus are normal or near normal for end stage renal disease patients. At the end of the second 12-week treatment period (during which time 1α-OH-vitamin D$_2$ treatment is suspended and replaced by placebo therapy), mean serum PTH values markedly increase, reaching pretreatment levels. This study demonstrates that: (1) 1α-OH-vitamin D$_2$ is effective in reducing serum PTH levels, and (2) 1α-OH-vitamin D$_2$ is safer than currently used therapies, despite its higher dosages and concurrent use of high levels of oral calcium phosphate binder.

The foregoing examples demonstrate that 1α-OH-vitamin D$_2$ is effective in preventing or restoring the loss of bone mass or bone mineral content while being substantially less toxic than 1α,25-(OH)$_2$-vitamin D$_3$ and 1α-OH-vitamin D$_3$. It is to be understood that although the foregoing examples detail the use of 1α-OH-vitamin D$_2$, other compounds within the scope of the claims may be readily utilized in the treatment of this invention with essentially equivalent results. For example, 1α,24(S)-(OH)$_2$-vitamin D$_2$ shows activity equivalent to 1α,24(R)-(OH)$_2$-vitamin D$_3$ and is also significantly less toxic than its vitamin D$_3$ counterpart. Also included within the scope of the claims would be administration of effective dosages of the analog of formula (I) in conjunction with administration of other hormones or other agents which have been shown to stimulate bone formulation in subjects experiencing or tending toward loss of bone mass or bone mineral content.

Such hormones or other agents may include conjugated estrogens or their equivalents, calcitonin, biphosphonates, calcium supplements, cobalamin, pertussis toxin and boron. Possible dose ranges for these co-administered agents are provided in Table 1.

TABLE 1

Possible Oral Dose Ranges for Various Agents Co-Administered With 1α-Hydroxyvitamin D$_2$

| Agent | Dose Ranges | | |
|---|---|---|---|
| | Broad | Preferred | Most Preferred |
| Conjugated Estrogens or Equivalent (mg/day) | 0.3–0.5 | 0.4–2.4 | 0.6–1.2 |
| Sodium Fluoride (mg/day) | 5–150 | 30–75 | 40–60 |
| Calcitonin (IU/day) | 5–800 | 25–500 | 50–200 |
| Biphosphonates | 50–2000 | 100–1500 | 250–1000 |
| Calcium Supplements (mg/day) | 250–2500 | 500–1500 | 750–1000 |
| Cobalamin (μg/day) | 5–200 | 20–100 | 30–50 |
| Pertussis Toxin (mg/day) | 0.1–2000 | 10–1500 | 100–1000 |
| Boron (mg/day) | 0.10–3000 | 1–250 | 2–100 |

Although the above examples detail dosage by mouth, it is to be understood that the compounds can also be administered in alternative fashions, including intranasally, transdermally, intrarectally, intravaginally, subcutaneously, intravenously, and intramuscularly.

In summary, the present invention provides therapeutic methods for lowering blood levels of parathyroid hormone which are secondary to end stage renal disease. The method in accordance with the present invention has significantly less resultant hypercalcemia and hyperphosphatemia.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

We claim:

1. A method for lowering or maintaining lowered serum parathyroid hormone in human patients suffering from hyperparathyroidism secondary to end stage renal disease, comprising: administering to said patients an effective amount of a vitamin D analog to lower and maintain lowered serum parathyroid hormone levels, said analog comprising formula (I):

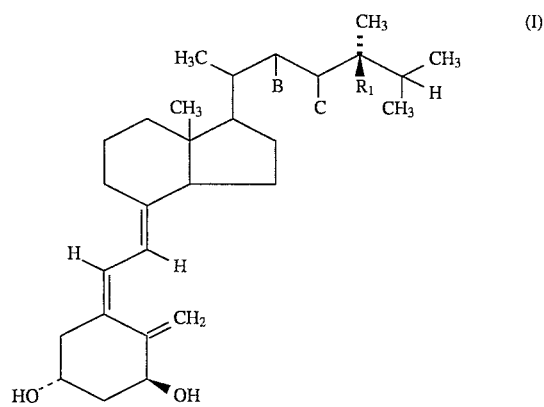

wherein B and C are either hydrogen or a carbon-carbon double bond between C$_{22}$ and C$_{23}$; and R$_1$ is hydrogen or hydroxyl provided that when B and C are a double bond, R$_1$ is hydrogen.

2. The method according to claim 1, wherein said analog of formula (I) is 1α-OH-vitamin D$_2$; 1α-OH-vitamin D$_4$; or 1α,24(R)-(OH)$_2$-vitamin D$_4$.

3. The method of claim 2 wherein said analog comprises a dosage of 1 to about 100 μg/week.

4. The method of claim 1 wherein said analog, in solution, in a liquid vehicle ingestible by and nontoxic to said patients, is administered orally in encapsulated form.

5. The method of claim 1, wherein said administration of said analog is parenteral.

6. The method of claim 5 wherein said administration is by subcutaneous, intramuscular, or intravenous injection, nasopharyngeal or mucosal absorption, or transdermal absorption.

7. The method of claim 2, wherein said analog is 1α-OH-vitamin D2.

8. The method of claim 2, wherein said analog is 1α, 24-(OH)$_2$-vitamin D2.

9. A method of treating a human to alleviate or prevent the pathological effects of hyperparathyroidism secondary to end stage renal disease, wherein the method comprises administering orally to said human, in need thereof, a vitamin D analog selected from the group consisting of 1α-OH-vitamin D$_2$; 1α-OH-vitamin D$_4$; and 1α,24(R)-(OH)$_2$-vitamin D$_4$ wherein said compound is administered to said human in an amount sufficient to lower serum parathyroid hormone levels as measured by blood serum level of parathyroid hormone over time after ingestion in said human to thereby alleviate or prevent said effects.

* * * * *

UNITED STATES PATENT AND TRADEMARK OFFICE
CERTIFICATE OF CORRECTION

PATENT NO. : 5,602,116
DATED : February 11, 1997
INVENTOR(S) : Knutson et al.

It is certified that error appears in the above-indentified patent and that said Letters Patent is hereby corrected as shown below:

Title page:
In the related U.S. Application Data field [63] on the face of the patent, in line 3, delete "Mar. 5, 1992" and substitute --Dec. 17, 1991--.

Column 1, line 7, delete "Mar. 5" and substitute --Dec. 17--.

Column 1, line 8, delete "1992" and substitute --1991--.

Signed and Sealed this

Tenth Day of March, 1998

Attest:

BRUCE LEHMAN

*Attesting Officer*      *Commissioner of Patents and Trademarks*

UNITED STATES PATENT AND TRADEMARK OFFICE
CERTIFICATE OF CORRECTION

PATENT NO.   : 5,602,116
DATED        : February 11, 1997
INVENTOR(S)  : Knutson et al.

It is certified that error appears in the above-identified patent and that said Letters Patent is hereby corrected as shown below:

Column 13,
Line 44, Table 1, the listing "Biphosphonates" should read -- Biphosphonates (mg/day) --.

Signed and Sealed this

Eighteenth Day of June, 2002

Attest:

JAMES E. ROGAN
Attesting Officer   Director of the United States Patent and Trademark Office